(12) United States Patent
Koth

(10) Patent No.: US 12,214,120 B2
(45) Date of Patent: Feb. 4, 2025

(54) MEDICAL DEVICE WITH IMPROVED DESUFFLATION

(71) Applicant: W.O.M. World of Medicine GmbH, Berlin (DE)

(72) Inventor: Yves Koth, Berlin (DE)

(73) Assignee: W.O.M. World of Medicine GmbH, Berlin (DE)

( * ) Notice: Subject to any disclaimer, the term of this patent is extended or adjusted under 35 U.S.C. 154(b) by 387 days.

(21) Appl. No.: 17/236,828

(22) Filed: Apr. 21, 2021

(65) Prior Publication Data

US 2021/0361886 A1    Nov. 25, 2021

Related U.S. Application Data

(63) Continuation of application No. 16/470,290, filed as application No. PCT/DE2017/000428 on Dec. 18, 2017, now abandoned.

(30) Foreign Application Priority Data

Dec. 16, 2016  (DE) .......................... 102016014980.9

(51) Int. Cl.
  *A61M 13/00*  (2006.01)
  *A61B 17/34*  (2006.01)

(52) U.S. Cl.
  CPC ....... *A61M 13/003* (2013.01); *A61B 17/3474* (2013.01); *A61M 2202/02* (2013.01);
  (Continued)

(58) Field of Classification Search
  CPC . A61B 17/3474; A61B 2218/008; A61F 9/00; A61F 9/00736; A61M 13/003;
  (Continued)

(56) References Cited

U.S. PATENT DOCUMENTS

| 3,954,920 A | 5/1976 | Heath |
| 5,246,419 A | 9/1993 | Absten |

(Continued)

FOREIGN PATENT DOCUMENTS

| DE | 4219859 | 12/1993 |
| DE | 4339876 | 5/1995 |

(Continued)

OTHER PUBLICATIONS

PCT International Search Report and Written Opinion dated Mar. 28, 2018 for PCT Application No. PCT/DE2017/000428.
(Continued)

*Primary Examiner* — Kami A Bosworth
*Assistant Examiner* — Avery Smale
(74) *Attorney, Agent, or Firm* — McCarter & English, LLP

(57) ABSTRACT

The present disclosure is directed to an insufflator which includes a controller, an insufflation line, a desufflation line, and one pressure sensor and one volume flow sensor associated with each of the insufflation line and the desufflation lines. The insufflation line is in fluid communication with a gas source and the desufflation line in fluid communication with a suction pump. Wherein the controller controls ventilation of a gas present in a patient by adjusting an amount of suction in the desufflation line as a function of pressure measurements obtained from the pressure sensors associated with the insufflation line and the desufflation line. Additionally, the controller includes an activation blocking system that prevents suction in the desufflation line when a pressure measured by means of the pressure sensor associated with the insufflation line is lower than a preset threshold value. Still further, the activation blocking system further prevents suction in the desufflation line when the pressure measured by means of the pressure sensor associated with the insuf- (Continued)

flation line and a pressure measured by means of the pressure sensor associated with the desufflation line are not identical.

19 Claims, 4 Drawing Sheets

(52) U.S. Cl.
CPC ............... *A61M 2205/3334* (2013.01); *A61M 2205/3337* (2013.01); *A61M 2205/3344* (2013.01)

(58) Field of Classification Search
CPC .. A61M 2205/3344; A61M 2205/3334; A61M 2202/02; A61M 13/00; A61M 13/006; A61M 2005/006; A61M 5/168; A61M 5/16877; A61M 5/16886; A61M 5/172; A61M 5/1723; A61M 5/484; A61M 2205/3331; A61M 1/77; A61M 1/772; A61M 1/777

See application file for complete search history.

(56) References Cited

U.S. PATENT DOCUMENTS

| | | |
|---|---|---|
| 5,411,474 A | 5/1995 | Ott et al. |
| 5,476,447 A | 12/1995 | Noda et al. |
| 5,558,084 A | 9/1996 | Daniell et al. |
| 5,588,423 A | 12/1996 | Smith |
| 5,800,381 A | 9/1998 | Ognier |
| 6,010,118 A | 1/2000 | Milewicz |
| 6,068,609 A | 5/2000 | Ott et al. |
| 6,299,147 B1 | 10/2001 | Mitter |
| 6,299,592 B1 | 10/2001 | Zander |
| 6,349,722 B1 | 2/2002 | Gradon |
| 6,584,972 B2 | 7/2003 | McPhee |
| 6,592,543 B1 | 7/2003 | Wortrich et al. |
| 6,598,604 B1 | 7/2003 | Seakins |
| 6,745,766 B2 | 6/2004 | Fini |
| 6,827,340 B2 | 12/2004 | Austin et al. |
| 6,842,314 B2 | 1/2005 | Sasaki et al. |
| 6,968,841 B2 | 11/2005 | Fini |
| 6,976,489 B2 | 12/2005 | Mantell et al. |
| 7,040,315 B1 | 5/2006 | Stromberg |
| 7,066,902 B1 | 6/2006 | Ott et al. |
| 7,204,248 B2 | 4/2007 | Enk |
| 7,250,035 B1 | 7/2007 | Ott et al. |
| 7,322,566 B2 | 1/2008 | Anthony |
| 7,425,210 B2 | 9/2008 | Sweeney et al. |
| 7,449,007 B2 | 11/2008 | Ott et al. |
| 7,455,653 B2 | 11/2008 | Ott et al. |
| 7,476,212 B2 | 1/2009 | Spearman et al. |
| 7,647,925 B2 | 1/2010 | Mantell et al. |
| 7,731,704 B2 | 6/2010 | Ott et al. |
| 7,744,557 B2 | 6/2010 | Ott et al. |
| 7,762,251 B2 | 7/2010 | Mantell et al. |
| 7,811,253 B2 | 10/2010 | Hart et al. |
| 7,918,816 B2 | 4/2011 | Ott et al. |
| 7,975,687 B2 | 7/2011 | Grundler et al. |
| 7,997,270 B2 | 8/2011 | Meier |
| 8,091,546 B2 | 1/2012 | Mantell et al. |
| 8,118,769 B2 | 2/2012 | Diemunsch |
| 8,133,196 B2 | 3/2012 | Hart et al. |
| 8,147,442 B2 | 4/2012 | Ott et al. |
| 8,181,940 B2 | 5/2012 | Payne et al. |
| 8,206,337 B2 | 6/2012 | Blackhurst et al. |
| 8,211,052 B1 | 7/2012 | Ott et al. |
| 8,240,306 B2 | 8/2012 | Cortez, Jr. et al. |
| 8,269,638 B2 | 9/2012 | Lloyd et al. |
| 8,333,195 B2 | 12/2012 | Cortez, Jr. et al. |
| 8,356,593 B2 | 1/2013 | Cortez, Jr. et al. |
| 8,444,591 B2 | 5/2013 | Temple |
| 8,544,461 B2 | 10/2013 | Grundler et al. |
| 8,608,715 B2 | 12/2013 | Roberts et al. |
| 8,608,816 B2 | 12/2013 | Palmerton et al. |
| 2002/0072700 A1 | 6/2002 | Mantell et al. |
| 2002/0139367 A1 | 10/2002 | McPhee |
| 2003/0181857 A1 | 9/2003 | Blake et al. |
| 2004/0154617 A1 | 8/2004 | Enk |
| 2005/0107766 A1 | 5/2005 | Ott et al. |
| 2005/0107767 A1 | 5/2005 | Ott et al. |
| 2005/0113795 A1 | 5/2005 | Ott et al. |
| 2005/0113797 A1 | 5/2005 | Ott et al. |
| 2006/0033223 A1 | 2/2006 | Mantell et al. |
| 2006/0052742 A1 | 3/2006 | Ott et al. |
| 2006/0129098 A1 | 6/2006 | Hart et al. |
| 2006/0151624 A1 | 7/2006 | Grundler et al. |
| 2006/0184096 A1 | 8/2006 | Ott et al. |
| 2007/0000300 A1* | 1/2007 | Diemunsch ......... A61M 13/003 600/300 |
| 2007/0107726 A1 | 5/2007 | Mantell et al. |
| 2007/0249990 A1 | 10/2007 | Cosmescu |
| 2010/0163044 A1 | 7/2010 | Mantell et al. |
| 2010/0241061 A1 | 9/2010 | Ott et al. |
| 2011/0028890 A1 | 2/2011 | Hart et al. |
| 2011/0106001 A1 | 5/2011 | Ott et al. |
| 2011/0166506 A1 | 7/2011 | Ott et al. |
| 2011/0230820 A1 | 9/2011 | Lillis et al. |
| 2011/0288474 A1 | 11/2011 | Ott et al. |
| 2011/0306925 A1 | 12/2011 | Mantell et al. |
| 2012/0074601 A1 | 3/2012 | Payne et al. |
| 2012/0172790 A1 | 7/2012 | Hart et al. |
| 2012/0238947 A1 | 9/2012 | Ott et al. |
| 2013/0211282 A1 | 8/2013 | Bunch |
| 2013/0249697 A1 | 9/2013 | Lloyd et al. |
| 2013/0255670 A1 | 10/2013 | Ott |
| 2014/0257172 A1* | 9/2014 | Yalamanchili ...... A61M 3/0208 604/22 |
| 2016/0041025 A1 | 2/2016 | Haynes |
| 2016/0106934 A1* | 4/2016 | Hiraga ................ A61B 1/3132 604/26 |
| 2016/0106952 A1* | 4/2016 | Mastri .................... A61M 1/80 604/26 |

FOREIGN PATENT DOCUMENTS

| | | | |
|---|---|---|---|
| DE | 102013016063 | 4/2015 | |
| DE | 102015000845 | 7/2016 | |
| DE | 102015000845 A1 * | 7/2016 | ............ A61M 13/00 |
| DE | 102016014980 | 6/2018 | |
| WO | WO 1996/001132 | 1/1996 | |
| WO | WO 2004/009167 | 1/2004 | |
| WO | WO 2011/041387 | 4/2011 | |
| WO | WO 2016/119773 | 8/2016 | |

OTHER PUBLICATIONS

U.S. Appl. No. 16/470,290, filed Jun. 17, 2019, US 2019-0307972 A1.
PCT/DE2017/000428, Dec. 18, 2017, WO/2018/108200.

* cited by examiner

MEDICAL DEVICE WITH IMPROVED DESUFFLATION

CROSS-REFERENCE TO REFLATED APPLICATIONS

This application is a continuation of U.S. patent application Ser. No. 16/470,290, filed on Jun. 17, 2019, entitled MEDICAL PUMP WITH IMPROVED DESUFFLATION, which is a national stage application based on PCT International Application No. PCT/DE2017/000428, filed on Dec. 18, 2017, claiming the benefit of priority to German Patent Application No. DE 10 2016 014980.9 filed on Dec. 16, 2016, the entire contents of each of these applications are hereby incorporated by reference.

FIELD

The present invention relates to medical device with improved desufflation, which includes an insufflator for laparoscopy and a suction pump, the suction pump being connected to the patient by means of a separate hose and permitting a controlled ventilation.

BACKGROUND

Laparoscopy a medical procedure, wherein the abdomen and the organs therein can visually be examined. For this purpose, commonly, small skin incisions (0.3 to 2 centimeters) are made in the abdominal wall, and a trocar is introduced therethrough, which in turn can accommodate an optical device. With the aid of a special endoscope (laparoscope), the abdomen can be inspected. In diagnostic laparoscopy, the abdomen is solely visually inspected, and in therapeutical laparoscopy, surgeries can also be performed.

Commonly, at the beginning of the laparoscopy, the abdomen is filled with gas, in order to establish pneumoperitoneum. For this purpose, different gases have already been used, such as air, nitrogen or carbon dioxide ($CO_2$). The use of carbon dioxide gas has proven particularly well.

After the end of the surgery, the introduced gas has to be removed again (ventilation or desufflation). Today, this is made in an uncontrolled manner by opening a trocar port. Thereby, in particular the following problems are caused:

1) The gas present in the patient is discharged in a non-filtered state into the operating room. Thus, surgery personnel is directly exposed to the poisonous combustion gases.
2) By the uncontrolled ventilation, there is a higher risk of $CO_2$ remaining in the patient. By the thus necessary absorption of the $CO_2$ by the body, often a post-operative pain is caused ("shoulder pain").
3) By the uncontrolled ventilation, the abdomen is collapsing excessively quickly.

The insufflation devices described in prior art that comprise suction devices (e.g., DE4219859 A1, WO 2004/009167 A1 or WO 2011/041387 A1) are not suitable for ventilation, for safety reasons.

It is the object of the present invention to permit a controlled and safe desufflation of the patient and to avoid the mentioned drawbacks.

SUMMARY

This object is achieved by the subject matter of the patent claims, i.e., an insufflation device with a suction pump and an insufflation and a separate desufflation line, wherein in the insufflation as well as in the desufflation line a pressure sensor and a volume flow sensor is provided, so that the pressures in two conduits can be measured at the same time.

the object is in particular achieved by an insufflation device for use in medical engineering comprising
an insufflator for gas supply with a gas source,
a controller unit,
an insufflation line and a separate desufflation line,
wherein the desufflation line is connected to a suction pump,
wherein the insufflation line and the desufflation line have one pressure sensor and one volume flow sensor each,
wherein the insufflator comprises a device for controlled ventilation of the gas present in the patient,
wherein the controller unit controls the power of the suction pump as a function of the pressure measurement of the pressure sensors,
wherein the controller unit contains an activation blocking system that prevents an activation of the suction pump, when the pressure measured by means of the pressure sensor in the insufflation line is lower than a preset threshold value,
wherein the activation blocking system further prevents an activation of the suction pump, when the pressure measured by means of the pressure sensor in the insufflation line and the pressure measured by means of the pressure sensor in the ventilation line are not identical.

DETAILED DESCRIPTION OF PREFERRED EMBODIMENTS

Figure 1:
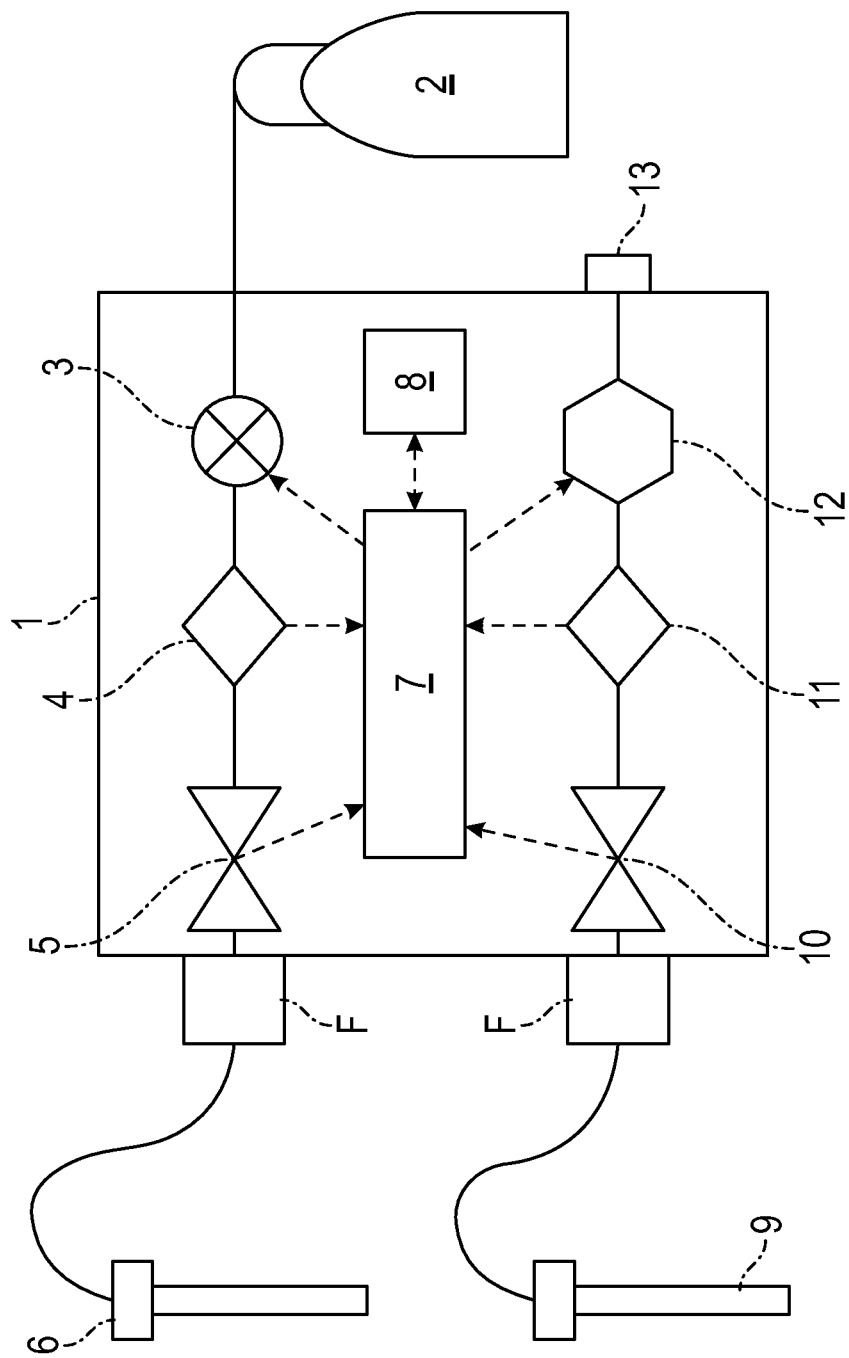
FIG. 1 shows an embodiment of an insufflator according to the invention.

In order to enable a desufflation, the insufflator is connected to the patient by means of two hoses. The first hose is used for insufflation. Gas is supplied to the patient during the surgery, in order to be able to, build up the pressure in the abdomen. Furthermore, the abdominal pressure measurement is performed through this line. A second hose may already be connected to the patient during the surgery, in order, instance, to implement a combustion gas discharge (FIG. 1).

As suction pumps can be used electronically controlled pumps, as described, for instance, in the device of DE 102013016063 or similar documents.

Figure 2:
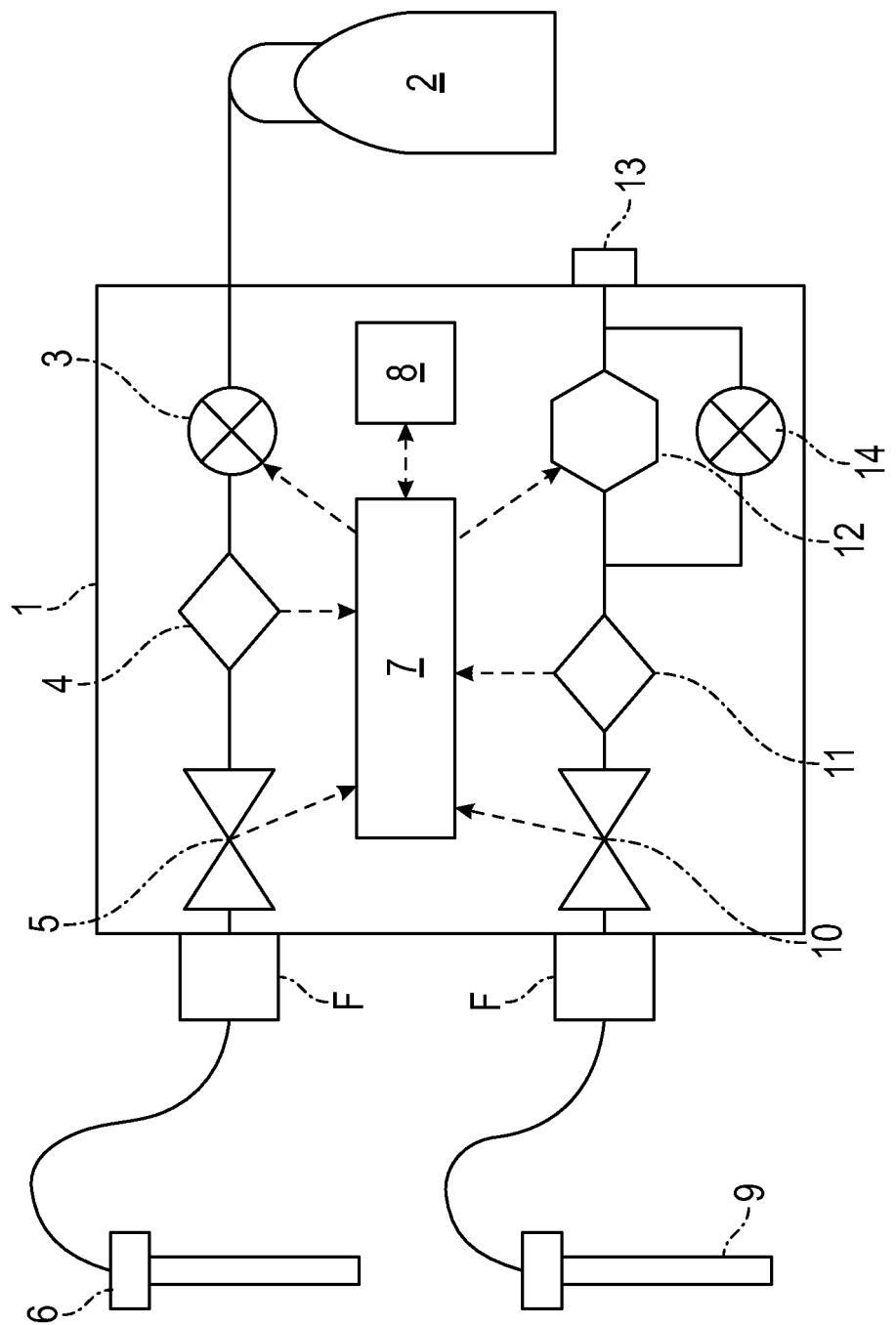
FIG. 2 shows a device according to further embodiment of the invention, wherein the suction pump is continuously working and the suction power is controlled by a bypass valve.

Alternatively, for instance, the suction pump may be controlled via a bypass valve (FIG. 2). For this purpose, for instance the pump may be preset to a certain power, which is to the greatest extent constant, and the control of the power is then performed via the bypass valve.

Figure 3:
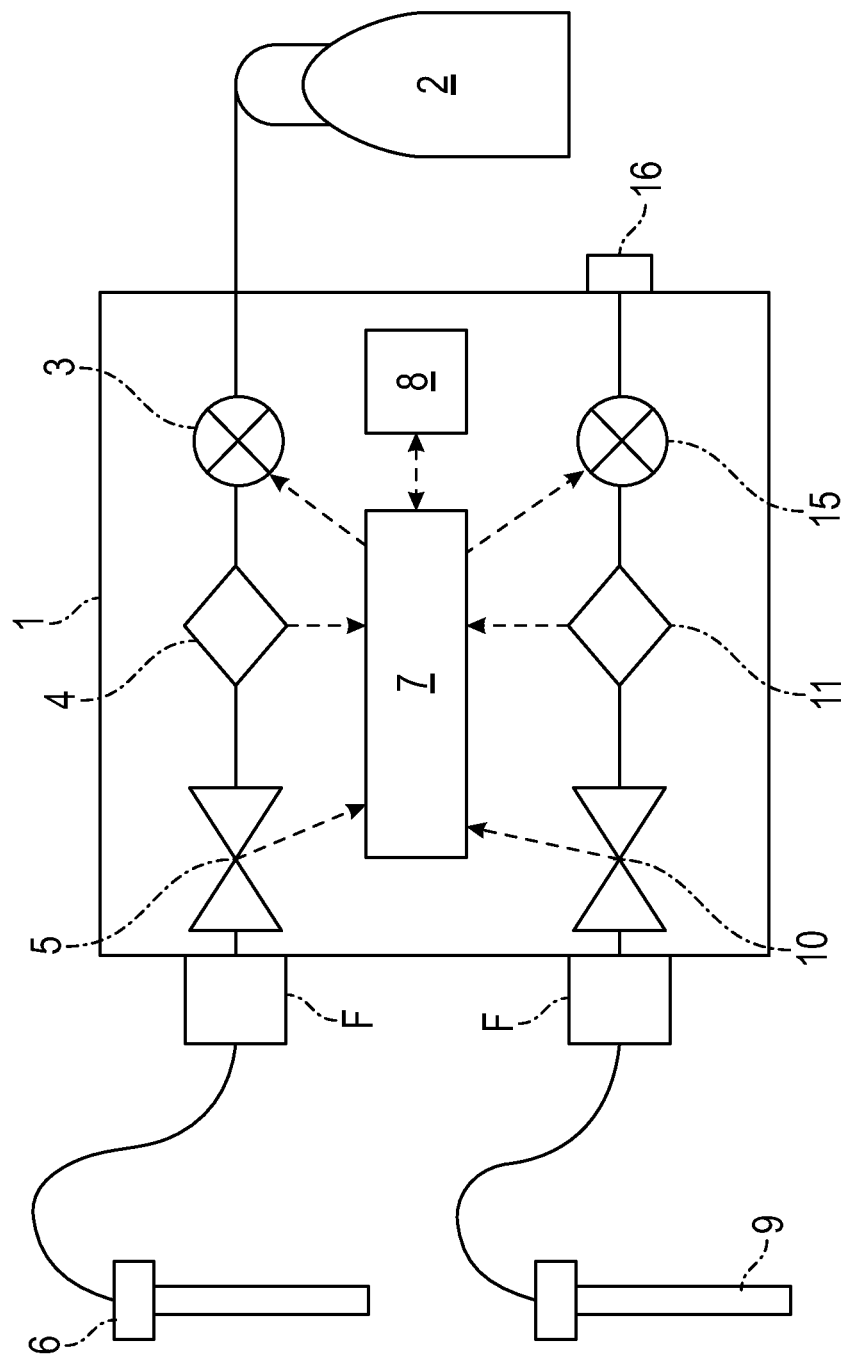
FIG. 3 shows another embodiment of the device according to the invention.

Further alternatively, a control valve may also be positioned directly in the ventilation line (FIG. 3). In this way, even external pumps may be used, for instance the all exhaust system existing in the operating room. The controller unit of the insufflator then controls the suction power via the shown control valve.

After stopping the insufflation, the insufflator offers the user the possibility to start the desufflation. When starting the desufflation process, the insufflator first checks the measured abdominal pressure via the insufflation line. If it is lower than an adjustable threshold value (<5 mmHg, preferably <3 mmHg), an activation blocking system prevents the start of the desufflation. The mentioned threshold value may be preset in the device. In particular embodiments of the invention, a selector switch or another selection device may be provided, by means of which the threshold value can be preset pre-operatively by the staff. If the measured abdominal pressure is higher than the preset threshold value, then abdominal pressure measured via the insufflation line is compared to the measured pressure in the ventilation line. If this is identical, it can be assumed that both hoses are connected to the patient. The two measured pressure values are assumed as identical, when their difference is smaller than 2 mmHg.

When these conditions are met, the suction pump can be activated. For safety reasons, the suction must not be too high, however, it should not be too mall, either, in order not to unnecessarily prolong the treatment. As a reasonable suction rate, 1 to 5 l/min. has been found, preferably approx. 3 l/min.

Further, the abdominal pressure is monitored via the insufflation line. Once the abdominal pressure is below a certain limit (e.g., 5, 4 or 3 mmHg), the desufflation stopped. The pressure limit (of e.g., 5, or 3 mmHg) may be preset in the device. Usually, a selector switch or another selection device is provided, by means of which the pressure limit can be preset by the staff before the surgery.

When, during the desufflation, the insufflation line cannot measure correctly the abdominal pressure anymore by a closure (e.g., by closing the stop cock at the trocar) or by a missing connection (e.g., early removal of the trocar), there will be a risk of too late an deactivation of the desufflation and thus of a negative pressure in the patient.

In the patent of Northgate U.S. Pat. No. 6,299,592, a method is described, how to detect an obstruction in the insufflation line. Therein, however, a continuous insufflation in the insufflation line takes place. Since an additional supply of gas during the suction is contra-productive, a different method is described in the following, in order to guarantee safety.

In the device according to the invention, the desufflation is interrupted in an interval-like manner. After turning the suction pump off, a certain time is waited, until pressure balancing has occurred. This depends, among other things, on the flow resistance, and is variable depending on the specific application. In order, on the one hand, to quickly reduce the abdominal pressure and on the other hand, to guarantee the waiting time for pressure balancing, it should preferably be waited dynamically. The end of the waiting time is reached, when a stable pressure exists on the suction side. Subsequently, it is tested whether the measured abdominal pressure in the insufflation line corresponds to the measured pressure in the desufflation line. When this is not the case, the desufflation is stopped. Otherwise, the desufflation continued.

At the beginning of the desufflation, the time interval, in which sucking occurs, is for instance between 10 and 1 seconds, particularly preferably 5 to 3 seconds. The measuring interval typically is between 5 and 0.5 seconds.

Should a larger leakage in the area of the abdomen (e.g., by another trocar) or a small volume in the abdomen exist, there is, however, still the risk, to generate an underpressure in the patient. The algorithm described above will detect in firm intervals (e.g., every 3 seconds) only the synchronism of the two pressure sensors. This interval is too long for those cases in order to safely detect an underpressure. Shortening the intervals will lead to an insufficient suction rate.

For this reason, a plausibility test has to be performed during the active ventilation. If the abdominal pressure in relation to the sucked-off volume decreases too slowly during the suction process (e.g., more than 0.3 liters/mmHg as an expected value for an average patient), the desufflation is interrupted. This volume is determined with the existing sensor for volume flow measurement.

In a preferred embodiment of the invention, the abdominal pressure rise during the insufflation of the patient is determined, is put in a relation to the insufflated volume and is stored. In this way, it can for instance be determined that for a pressure rise of 1 mmHg a gas flow of 0.35 liter is required. This value is stored in the controller unit. For the desufflation of the same patient, it can be expected, that per 0.35 liter pumped-off gas, a pressure drop of 1 mmHg will occur (expected value: 0.35 l/mmHg). During the desufflation, the pressure drop per gas volume is monitored. Should the expected value significantly be exceeded or fallen below (e.g., by more than 20%), the desufflation will automatically be stopped.

Alternatively, a continuous verification of the abdominal pressure with the aid of the pressure sensor on the suction side can be performed. This verification is based on a mathematical observer model (e.g., Luenberger observer) that has been designed based on a model in control theory. Such models are described in prior art (WO 2016/119773 A1) and thus do not need any further explanations here. In this way, during ventilation already, a synchronism of the two pressure sensors can be monitored and the desufflation can be interrupted in case of a deviation.

Besides a closure in the insufflation line, a closure in the suction line must also be detected, in order not to cause any tissue damage (e.g., sucking organs). On the suction side, in case of the reduction of the sucked-off volume flow or of too high an underpressure, a closure on the suction side is detected, and the desufflation is also interrupted. In these cases, it is afterwards checked whether the measured abdominal pressure in the insufflation line corresponds to the measured pressure in the desufflation line. When this is not the case, the desufflation is stopped. Otherwise, the desufflation is continued.

Additionally, ventilation can be performed by means of special suction trocars. Classical trocars essentially pin-type (cylindrical) tubes with a circular opening that is positioned in the abdomen of the patient, and with various connection possibilities outside of the patient. With ventilation of gas during desufflation, there is a risk that the suction opening adheres to sensitive tissue parts. This risk is reduced, when the trocars are configured such that the cylinder wall in the end portion comprises openings. In a preferred embodiment, the trocar contains recesses in the area of the opening aeration (FIG. 4).

FIG. 1 shows an embodiment of an insufflator according to the invention. The insufflator (1) is connected to a gas source (2), e.g., in the form of a $CO_2$ gas bottle. Via a proportional valve (3), a pressure sensor (4), a volume flow sensor (5) and a filter (F), the insufflation trocar (6) is introduced. The separate desufflation trocar (9) is connected via a hose to the insufflator, the gas flow first being directed again through a filter (F), a volume flow sensor (10), a pressure sensor (11) to a suction pump (12). The output of the suction pump leads to a device outlet (13). The device outlet (13) may of course be provided with an additional filter. The measured data of the pressure sensors (4, 11) and of the volume flow sensors (5, 10) are transmitted to the calculation unit (7) with a connected memory (8). The calculation unit (7) controls the proportional valve (3) and the suction pump (12). As is familiar for those skilled in the art, the positions of the pressure sensors and the volume flow sensors may also be located at other positions: it is of course possible that the insufflation flow is first directed through the volume flow sensor (5) and then through the pressure (4). In a similar way it is possible that the volume flow sensor (10) of the desufflation line is positioned behind the suction pump (12), in the direction of flow.

FIG. 2 shows a device according to the invention, wherein the suction pump (12) is continuously working and the suction power is controlled by a bypass valve (14). The bypass valve (14) is also controlled via the calculation unit (7) (not Shown FIG. 2).

FIG. 3 shows another variant of the device according to the invention. Herein, instead of a suction pump, a connection port (16) for an external pump is provided in the device. Many hospitals are equipped with corresponding pumps that can be used for the intended application of an insufflator according to the invention. In this case, only a control valve (15) is required, in order to control the suction rate of the external pump (not shown).

Figure 4A:
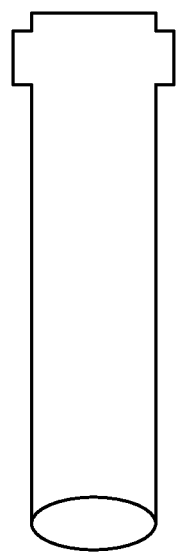
FIG. 4a shows a conventional (cylindrical) trocar with corresponding connection ports.
Figure 4B:
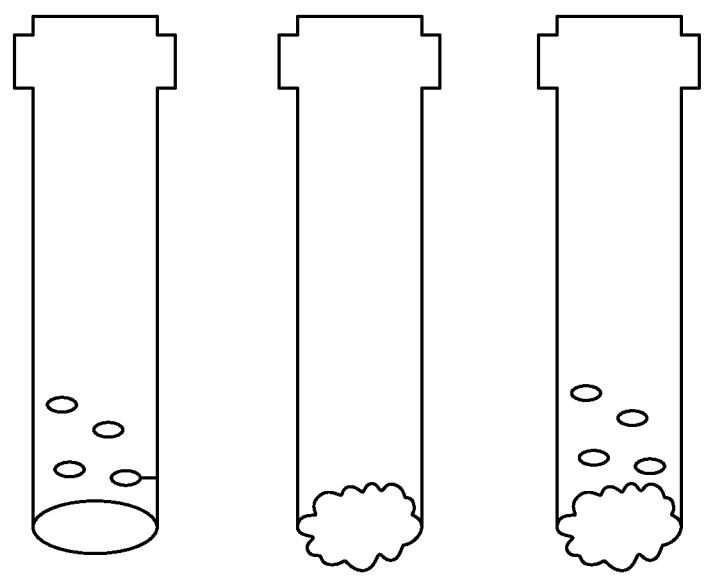
FIG. 4b shows different suction trocars according to embodiments of the invention that either have openings in the cylinder wall (on the left) or are irregularly configured in the area of the cylinder (middle) or have openings in the cylinder wall as well as an irregularly shaped end piece (on the right).

FIG. 4 shows embodiments of suction trocars. FIG. 4a shows a conventional (cylindrical) trocar with corresponding connection ports. FIG. 4b shows different suction trocars according to the invention that either have openings in the cylinder wall (on the left) or are irregularly configured in the area of the cylinder (middle) or have openings in the cylinder wall as well as an irregularly shaped end piece (on the right). It is crucial, herein, that the end of the cylinder does not sit on tissue and cannot adhere thereto. By the provided openings, such an adhesion is effectively prevented.

The individual components of the device according to the invention are mostly known from earlier documents, such as, e.g., U.S. Pat. Nos. 6,299,592, 5,411,474, WO1996001132A1, WO 2011041387A1, U.S. Pat. No. 5,800,381, DE 4219859B4, DE 102015000845A1, however not in conjunction with a device according to the invention, as defined by the claims. As a controller unit serves a correspondingly programmed microcomputer with respective memory and input and output devices. Volume flow sensors are already known from other medical devices (e.g., for breathing apparatus), so that they need not be explained here in more detail.

Those skilled in the art can implement alternative and/or supplementing embodiments of the invention without any inventive activity.

What is claimed is:

1. A medical device comprising:
an insufflator which includes a controller, an insufflation line, a desufflation line, and one pressure sensor and one volume flow sensor associated with each of the insufflation line and the desufflation line; the insufflation line in fluid communication with a gas source and the desufflation line in fluid communication with a suction pump;
wherein the controller controls ventilation of a gas present in a patient by adjusting an amount of suction in the desufflation line as a function of a pressure measurements obtained from the pressure sensor associated with the insufflation line and a pressure measurement obtained from the pressure sensor associated with the desufflation line,
wherein the controller activates the suction, and estimates an abdominal pressure of the patient using the pressure sensor of the desufflation line by means of a mathematical observer model and compares the estimated abdominal pressure to the pressure measurement of the pressure sensor in the insufflation line, wherein the suction remains activated only with identical values, effectively a difference smaller than 2 mmHg, between the estimated abdominal pressure and the pressure measurement of the pressure sensor in the insufflation line;
wherein the controller includes an activation blocking system that prevents the suction in the desufflation line when the pressure measurement by means of the pressure sensor associated with the insufflation line is lower than a preset threshold value, and
wherein the activation blocking system further prevents the suction in the desufflation line when the pressure measurement of the pressure sensor associated with the insufflation line and the pressure measurement of the pressure sensor associated with the desufflation line have values which are not identical.

2. The medical device according to claim 1, wherein the suction pump is contained within a housing for the insufflator.

3. The medical device according to claim 1, wherein the insufflator includes a connection port for communicating with the suction pump and the suction pump is external to the insufflator.

4. The medical device according to claim 3, wherein the insufflator includes a control valve for controlling a suction rate of the suction pump.

5. The medical device according to claim 1, wherein the preset threshold value is lower than 5 mm Hg.

6. The medical device according to claim 1, wherein the preset threshold value is lower than 3 mm Hg.

7. The medical device according to claim 1, wherein the controller cyclically pauses the suction, and during the suction pauses compares the pressure measurement of the pressure sensor associated with the insufflation line and the pressure measurement of the pressure sensor associated with the desufflation line, wherein the suction is activated again only with identical values of the pressure measurement of the pressure sensor associated with the insufflation line and the pressure measurement of the pressure sensor associated with the desufflation line.

8. The medical device according to claim 1, wherein the controller compares a sucked-off gas volume obtained using the volume flow sensor associated with the desufflation line to a decrease in the abdominal pressure and wherein the controller suspends the suction, when the comparison of the sucked-off gas volume to the decrease in the abdominal pressure does not correspond to an expected value.

9. The medical device according to claim 8, wherein the controller determines and stores the expected value of the comparison of the sucked off gas volume to the decrease in the abdominal pressure during an insufflation phase by measurement of a rise in the abdominal pressure to an insufflated volume during the insufflation phase.

10. The medical device according to claim 1, wherein the mathematical observer model is configured in a manner of a Luenberger observer.

11. The medical device according to claim 1, wherein the desufflation line is connected to a cylindrical trocar, the cylindrical trocar being configured such that the cylindrical trocar comprises recesses in a cylinder wall.

12. A method for controlled ventilation of a gas present in a patient after a surgery, by means of the medical device according to claim 1, the method comprising activating the suction via the controller only when:
   a) the pressure measurement of the pressure sensor associated with the insufflation line is higher than the preset threshold value, and b) when the pressure measurement of the pressure sensor associated with the insufflation line and the pressure measurement of the pressure sensor associated with the desufflation line are identical in value; wherein the controller pauses the suction and verifies the pressure the pressure measurement of the pressure sensor associated with the insufflation line and the pressure measurement of the pressure sensor associated with the desufflation line during the suction pauses; and the controller activates the suction pump and determines the abdominal pressure using the pressure sensor of the desufflation line, the pressure being estimated by the mathematical observer model and wherein the controller compares the estimated abdominal pressure to the pressure measurement of the pressure sensor in the insufflation line, wherein the suction remains activated only with identical values effectively a difference smaller than 2 mmHg, between the estimated abdominal pressure and the pressure measurement of the pressure sensor in the insufflation line.

13. The method according to claim 12, wherein the suction is performed at a suction rate of 1 to 5 l/min.

14. The method according to claim 12, wherein the suction is stopped once the abdominal pressure is 5, 4 or 3 mmHg.

15. The method according to claim 12, wherein the preset threshold value is larger than 5 mmHg.

16. The method according to claim 12, wherein the preset threshold value is larger than 3 mmHg.

17. The method according to claim 12, further including a step of providing the insufflator with a connection port for communicating with the suction pump and the suction pump is external to the insufflator.

18. The method according to claim 12, further including a step of providing the insufflator with a control valve for controlling a suction rate of the suction pump.

19. The method according to claim 12, wherein the mathematical observer model is configured in a manner of a Luenberger observer.

* * * * *